(12) United States Patent
Yuen et al.

(10) Patent No.: US 12,383,790 B2
(45) Date of Patent: Aug. 12, 2025

(54) INTEGRATED SPORTS TRAINING

(71) Applicants: William Yuen, Miami Beach, FL (US); Jack R. Yuen, Miami Beach, FL (US)

(72) Inventors: William Yuen, Miami Beach, FL (US); Jack R. Yuen, Miami Beach, FL (US)

(*) Notice: Subject to any disclaimer, the term of this patent is extended or adjusted under 35 U.S.C. 154(b) by 0 days.

(21) Appl. No.: 18/739,465

(22) Filed: Jun. 11, 2024

(65) Prior Publication Data
US 2024/0408444 A1 Dec. 12, 2024

Related U.S. Application Data

(63) Continuation of application No. 17/675,518, filed on Feb. 18, 2022, now Pat. No. 12,029,941.

(60) Provisional application No. 63/153,831, filed on Feb. 25, 2021.

(51) Int. Cl.
*A63B 24/00* (2006.01)
*A63B 71/06* (2006.01)

(52) U.S. Cl.
CPC ...... *A63B 24/0006* (2013.01); *A63B 71/0622* (2013.01); *A63B 2024/0015* (2013.01); *A63B 2220/34* (2013.01); *A63B 2220/40* (2013.01); *A63B 2220/836* (2013.01)

(58) Field of Classification Search
CPC ........... A63B 24/0006; A63B 71/0622; A63B 2024/0015; A63B 2220/34; A63B 2220/40; A63B 2220/836; A61B 5/1114; G16H 20/30; G06V 40/23
See application file for complete search history.

(56) References Cited

U.S. PATENT DOCUMENTS

| | | | |
|---|---|---|---|
| 8,419,560 B2* | 4/2013 | Amini | A63B 71/0622 |
| | | | 473/212 |
| 10,352,962 B2* | 7/2019 | Douglas | G06V 40/25 |
| 12,029,941 B2 | 7/2024 | Yuen | |
| 2011/0205535 A1 | 8/2011 | Soller et al. | |
| 2013/0018493 A1 | 1/2013 | Amini | |
| 2015/0045699 A1 | 2/2015 | Mokaya et al. | |
| 2018/0154215 A1* | 6/2018 | Ryu | G06V 40/23 |
| 2019/0358493 A1* | 11/2019 | Quatrochi | A61B 5/1118 |
| 2019/0374161 A1 | 12/2019 | Ly et al. | |

(Continued)

FOREIGN PATENT DOCUMENTS

| | | | | |
|---|---|---|---|---|
| EP | 2778612 A2 * | 9/2014 | | A63B 24/0062 |
| WO | WO 2022/182591 | 9/2022 | | |

OTHER PUBLICATIONS

PCT Application No. PCT/US2022/17007 International Search Report and Written Opinion dated Jun. 10, 2022.

(Continued)

*Primary Examiner* — Francis C Gray
(74) *Attorney, Agent, or Firm* — Polsinelli LLP

(57) ABSTRACT

A sports training system that uses several inertia measurement units (IMUs) to measure a user's motion while performing an action during a sport such as a golfer swing. The IMUs can have additional sensors connected to improve the system's ability to detect flaws in the user's motion. Furthermore, the system uses machine learning to detect and determine flaw in a user's motion from the IMU data. The data can be collected and set up on a user device while an instructor device provides feedback on the type of flaws and recommendations to improve.

21 Claims, 13 Drawing Sheets

(56) References Cited

U.S. PATENT DOCUMENTS

| | | | |
|---|---|---|---|
| 2020/0261023 A1* | 8/2020 | Werbin | A61B 5/01 |
| 2021/0245005 A1* | 8/2021 | Pao | A63B 24/0006 |
| 2021/0321875 A1 | 10/2021 | Fang | |
| 2022/0266091 A1* | 8/2022 | Yuen | G16H 80/00 |

OTHER PUBLICATIONS

U.S. Appl. No. 17/675,518, Office Action mailed Nov. 7, 2023.
KR Application No. 10-2023-7032579, Office Action dated May 15, 2025.

* cited by examiner

203

| Sensor Location | Sensor Type | Normal Range | Outside Range | Flag |
|---|---|---|---|---|
| Back foot (right leg for right-handed swing) | Pressure sensitive conductive sheet | 3 to 5 psi | >5 psi | Too much weight on back leg/foot |
| Front foot (left leg for right-handed swing) | Pressure sensitive conductive sheet | 3 to 5 psi | <3 psi | Too much weight on front leg/foot |
| Left foot; right foot (right-handed swing) | Pressure sensitive conductive sheet | 6 to 8 psi; 3 to 5 psi | <6psi; >5 psi | Too much weight on back leg/foot |

| Flaw | Suggestion | Lesson | Exercise/Stretch | Video |
|---|---|---|---|---|
| Too much weight on back leg/foot | Pressure sensitive conductive sheet | Weight_transfer.dat | Hamstring-quads stretch.dat | Video1.vid |
| Dropping back shoulder during swing | Keep shoulders level | Practicing_Level_swing.dat | Core-Strengthing.dat | Video2.vid |
| To tight of a grip | Loosen grip | Grip_practice_Lesson.dat | Grip strengthen-stretch.dat | Video3.vid |

FIG. 4

INTEGRATED SPORTS TRAINING

CROSS-REFERENCE TO RELATED APPLICATIONS

The present patent application is a continuation and claims the priority benefit of U.S. patent application Ser. No. 17/675,518 filed Feb. 18, 2022, which claims the priority benefit of U.S. provisional patent application 63/153,831 filed Feb. 25, 2021, the disclosures of which are incorporated by reference herein.

BACKGROUND OF THE INVENTION

1. Field of the Invention

The present disclosure is generally related to real-time sensor-based monitoring devices and associated methods for tracking and analyzing the motion of the body without the need for a human coach. More specifically, the present disclosure is related to using a sensor package or a suite of sensors that can be placed on different parts of the body, monitoring the sensor data is monitored, and analyzing the sensor data so as to provide a user feedback regarding how to adjust their movements to achieve different results.

2. Description of the Related Art

Every sport comes with its own set of challenges and complexities, especially when it comes to training and coaching. It is even more difficult to train when it comes to high-performance athletes. In addition to level of performance, the complexity of the sport itself will determine how difficult it is to train someone. For example, it is a lot easier to "pick up"/learn how to play table tennis than golf. Both sports require reasonable hand-eye coordination. However, golf further requires control over more details, such as pertains to grip (e.g., how much pressure and which fingers to apply pressure to the grip), stance, hip rotation, weight transfer, head position, elbow lock, wrist rotation, etc. Not only may there be additional physical factors to control, but such factors need to be coordinated and synchronized together just to get the ball off the ground. Current training tools only identify/improve certain aspects of one's game. It is not humanly possible, even for professional golf instructors, to be able to observe/analyze grip pressure or all the above-mentioned details all at once.

Not only can poor form and movement result in poor performance in a given physical activity, but in certain situations, a user may inflict harm or injure themselves during the activity. For example, a user lifting heavy weights can easily injure themselves using incorrect form or posture. Without a personal trainer or other knowledgeable observer to provide guidance, the user may not realize their potential danger. Understanding a user's movements in fitness such as weightlifting, yoga and other sports can help not only improve a user's performance but also prevent injury.

Using sensors in sports and health is well known in the industry. There are several fitness watches on the market for tracking user steps and heart rate, but these devices are limited in the amount of data they can provides and cannot really monitor a user's motion accurately. As such, current devices do not have the ability to monitor and analyze all the parameters of a user's real-time motion in enough detail to predict outcomes (e.g., success, failure, injury) and to make recommendations (e.g., as to adjustments). While some sensors or cameras may capture data and images, there are presently no systems available that can automatically capture and use such data and images to generate predictions and recommendations (particularly as to fine adjustments) across different physical activities There is therefore a need in the art for improved systems and methods of real-time sensor-based monitoring and analysis of physical movement.

SUMMARY OF THE CLAIMED INVENTION

Embodiments of the present invention may include a sensor package or a suite of sensors designed to fit in to a small form factor. Additional sensors connected to the package can be adapted to any sport or physical activity in which different parameters may be monitored. Any number of sensor packages could be placed at different points of the user's body depending on the sport and the movement that needs to be tracked. Additional sensors could be added or connected to the sensor package depending on their need and sport. Golf is an example where multiple sensor packages with some additional sensors connected could accurately analyze and predict a result of a user's swing. A golf swing has many different components, and a user may use several sensors to analyze their swing (e.g., a sensor package with sensors to be placed on their knees, waist, shoulders, in the club, on a glove, attached to the head, and in the shoes). The sensor packages in the shoes and gloves may have additional pressure sensor attached to monitor pressure.

BRIEF DESCRIPTION OF THE DRAWINGS

FIG. 2 illustrates an exemplary machine learning (ML) database for a given physical movement.

FIG. 4 illustrates an exemplary suggestion database.

DETAILED DESCRIPTION

Embodiments of the present invention may include a sensor package or a suite of sensors designed to fit in to a small form factor. Additional sensors connected to the package can be adapted to any sport or physical activity in which different parameters may be monitored. Any number of sensor packages could be placed at different points of the user's body depending on the sport and the movement that needs to be tracked. Additional sensors could be added or connected to the sensor package depending on their need and sport. Golf is an example where multiple sensor packages with some additional sensors connected could accurately analyze and predict a result of a user's swing. A golf swing has many different components, and a user may use several sensors to analyze their swing (e.g., a sensor package with sensors to be placed on their knees, waist, shoulders, in the club, on a glove, attached to the head, and in the shoes). The sensor packages in the shoes and gloves may have additional pressure sensor attached to monitor pressure.

Figure 1:
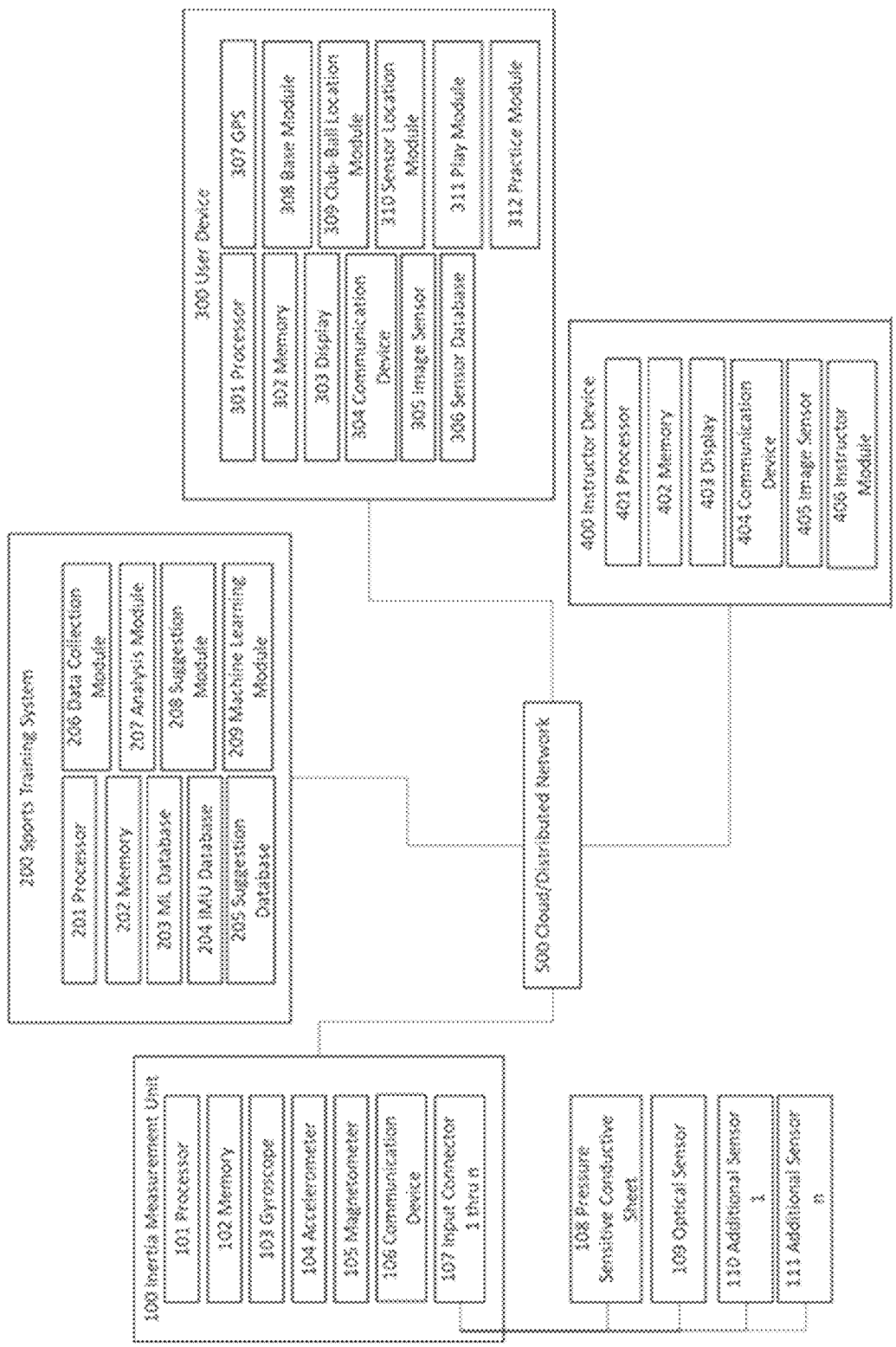
FIG. 1 illustrates an exemplary network environment in which a system for monitoring and analyzing physical movement may be implemented.

FIG. 1 illustrates an exemplary network environment in which a system for monitoring and analyzing physical movement may be implemented. The network environment of FIG. 1 may include an inertia measurement unit (IMU) 100. The IMU 100 is a suite of sensors designed to fit in a compact package which is then attached to a user, such as an athlete, to monitor the motion of the wearer. The system would further include several IMU 100 which a user would place on different parts of the body such as the arms, elbows, knees, waist, shoulders, head, feet, or hands. Further, the IMU 100 can also be placed within sports equipment such as inside a golf club head, shoes, or gloves (i.e. golf glove). Additionally, the IMU 100 allow additional sensors to be connected to adapt to different sports and allow for the collection of other types of data such a pressure data. The IMU 100, further includes a processor 101, a memory 102, a gyroscope 103, an accelerometer 104, a magnetometer 105, a communication device 106, and any number of input connector 1 thru n 107. Further, other sensors or data collection devices may be connected to the input connectors 1 thru n 107 such as a pressure sensitive conductive sheet 108, an optical sensor 109, additional sensor 1 110 and additional sensor n 111. A processor 101 may be used to execute an algorithms, code, or commands stored in the memory 102. The processor 101 may also be configured to decode and execute any instructions received from one or more other electronic devices, server(s), sensors, or other connected devices. The processor 101 may include one or more general purpose processors (e.g., INTEL® or Advanced Micro Devices® (AMD) microprocessors, ARM) and/or one or more special purpose processors (e.g., digital signal processors, Xilinx® System On Chip (SOC) Field Programmable Gate Array (FPGA) processor, and/or Graphics Processing Units (GPUs)). The processor 101 may be configured to execute one or more computer-readable program instructions, such as program instructions to carry out any of the functions described in this description. The memory 102 is used to store information used in a computing device or related computer hardware such as the IMU 100. The memory 102 may be a semiconductor memory or metal-oxide-semiconductor (MOS) memory where data is stored within MOS memory cell. Examples of non-volatile memory are flash memory (used as secondary storage) and ROM, PROM, EPROM and EEPROM memory (used for storing firmware such as BIOS). Examples of volatile memory are primary storage, which is typically dynamic random-access memory (DRAM), and fast CPU cache memory, which is typically static random-access memory (SRAM) that is fast but energy-consuming, offering lower memory areal density than DRAM. The Gyroscope 103 is a device used for measuring or maintaining orientation and angular velocity, such as the microchip-packaged MEMS gyroscopes found in electronic devices (sometimes called gyrometers). The accelerometer 104 is a device that measures proper acceleration. Proper acceleration is the acceleration (the rate of change of velocity) of a body. Two or more accelerometers 104 when coordinated with one another can measure differences in proper acceleration. The magnetometer 105 is a device that measures the direction, strength, or relative change of a magnetic field at a particular location. A compass is one such device, one that measures the direction of an ambient magnetic field, in this case, the Earth's magnetic field. The magnetometer 105 in the IMU 100 would provide directional data for any motion of a user. The communication device 106 is used for communicating data and commands to other IMU 100 or to other devices that are part of the system such as the sports training system 200, a user device 200 or an instructor device 400. The communication can be done though a wired connection or wirelessly user well know wireless communication devices and protocols such as Bluetooth, NFC, Wi-Fi standards, or cellular. Furthermore, the communication devices from at least two different IMUs 100 can be used to triangulate the location of a third IMU 100 by analyzing the communication signal. For example, an IMU 100 in both the shoes of a user could be used to determine the location of a golf club head that has a third IMU 100 in the club head. Allowing the system to determine the location of the club head and subsequently the location of the ball to ensure the user ball and club are in the correct position for the selected club. Based on the determined location, feedback can be provided to the user. Input connectors 1 thru n 107 represent at least one means of connecting external devices such as other sensors to the IMU 100. This would allow the IMU 100 to be adapted to other sports by allowing additional sensors to be connected. The input connectors 1 thru n 107 may include, but not limited to USB, USB-C, thunderbolt, 4- 6- or 8 pin connectors. There are many other known connection devices that are well known in the art. The pressure sensitive conductive sheet 108 is connected to the IMU 100 through the input connector 1 thru n 107. The pressure sensitive conductive sheet 108 is electrically conductive sheet that is flexible and can be incorporated into wearable items. For example, pressure sensitive sheets could be applied to or woven in to gloves or insoles of shoes. The sheets would be used to monitor pressure such as understanding a user's grip from a glove or tracking a user's weight distribution from the insole of the user's shoes. Specifically, the grip of a golfer on the club is very specific and can affect the accuracy of the swing, a pressure sensitive sheet in a golf glove can provide valuable data of the golfer's grip. In another embodiment pressure sensitive sheet may be in the insole of a user's shoe in other forms of clothing. The optical sensor 109 such as an image sensor, CMOS, infrared sensor, or other types of optical sensor used for capturing images. The optical sensor would connect to the IMU 100 through the input connector 1 thru n 107. The optical sensor can be used for visual tracking motion. For example, an optical sensor on the brim of a hat that points towards a user's face could be used to track a user's eye movement. Alternatively, the optical sensor can be pointed directly forward, i.e., if the athlete was looking straight then the optical sensor should be able to see the club or bat hit the ball at contact It is very difficult of an instructor to see a user's eye movement especially subtle glances or eye movements. For example, if an athlete takes their eye off the ball during a swing, even if that glance away is only a fraction of a second, that glance can have large impact on the accuracy of the athlete's swing. The additional sensor 1 110 and additional sensor n represent any number of additional sensors that could be attached to the IMU 100 through the input connector 1 thru n 107. The additional sensors allow for the IMU 100 to be adapted to other types of sensors that can customize the IMU for different sports. For example, a swimmer may add different flow rate sensors or monitors to understand the flow of water over their body. Further, the sports training system 200 includes a processor 201, a memory 202, a ML database 203, a IMU database 204, a suggestion database 205, a data collection module 206, an analysis module 207, a suggestion module 208, and a machine learning module 209. The sport training system 200 collects data the user device 300 or directly from the IMUs 100. The data is collected and analyzed, then visualizations are developed depending on the sport and sent back to both the user device 300 and the instructor device 400. The visualizations are then used by the user and instructors to provide feedback and improve the user's movement for the sport. The sports training system 200 further can provide automated feedback to a user to help improve their performance by comparing IMU 100 data and associated analysis to similar historical analysis which will have improvement tips, trick, exercises to help improve abnormalities found in the users motion. The processor 201 may include one or more general purpose processors (e.g., INTEL® or Advanced Micro Devices® (AMD) microprocessors, ARM) and/or one or more special purpose processors (e.g., digital signal processors, Xilinx® System On Chip (SOC) Field Programmable Gate Array (FPGA) processor, and/or Graphics Processing Units (GPUs)). The processor 201 may be configured to execute one or more computer-readable program instructions, such as program instructions to carry out any of the functions described in this description. The memory 202 is used to store information used in a computing device or related computer hardware. The memory 202 may be a semiconductor memory or metal-oxide-semiconductor (MOS) memory where data is stored within MOS memory cell. Examples of non-volatile memory are flash memory (used as secondary storage) and ROM, PROM, EPROM and EEPROM memory (used for storing firmware such as BIOS). Examples of volatile memory are primary storage, which is typically dynamic random-access memory (DRAM), and fast CPU cache memory, which is typically static random-access memory (SRAM) that is fast but energy-consuming, offering lower memory areal density than DRAM. The ML Database 203 stores historical or all known IMU data which the machine learning module uses to compare to determine potential issues or flaws with a user's swing. For example, the ML database 203 may store all data for flaws in a golfer's swing and what the associated remedies would be to fix the flaw. If a golfer has too much weight on his back leg and is slicing the ball, the ML database would have IMU 100 data associated with this and the related fix, trick or exercise to fix the issue of too much weight on the back leg. In another example, the IMU 100 located on a glove will use the gyroscope to detect if a user is over rotating or not rotating their hands or wrist which could cause the golf ball to slice or hook. The IMU Database 204 stores all the IMU data received from either the user device 300 or the IMU 100. The stored data would include any sensor data, time stamps, user information, type of sport the user is using the IMU 100 for. The suggestion database 205 stores suggested lessons, tips, tricks, corrections, and exercises to help correct a flaw or correction in a motion of a user (i.e. athlete) or prevent injuries. The suggestion data may come in the form of text, animation, or videos. The data collection module 206 communicates with the user device 300 and the IMUs 100 to collect and organize the data in the IMU Database 204. The analysis module 207 uses data stored in the IMU Database 204 and organized and normalizes the data based on the sport the IMUs 100 are being used for. It compares the IMU 100 data in the IMU Database 204 with data from what would be an ideal swing. The IMU 100 data from the IMU Database 204 can then be mapped and charts and visualizations created to show how the IMU data compares to normal or accurate motion. For example, IMU data from for a user's golf swing would be compared to an ideal or perfect golf swing. The ideal or perfect golf swing may be different for each user as every user has differences. The comparison will show where the user's IMU data (i.e. motion data) falls outside the normal ranges for an ideal or perfect swing. These differences in ranges from the IMU data and the ideal or perfect swing can then be mapped to visualizations. For example, a heat map could be created of the user's motion and animated. The heat map could be a 3D representation of the user's body and shows an animation of the user's swing and body position. The IMU data is then mapped to the 3D representation for the entirety of the swing. If the IMU data is outside certain ranges, it would display red on the 3D representation. This way a user or an instructor could see the issues related to the user's swing through the whole animation of the swing. Other charts and graphs could also be generated comparing the IMU data to the ideal or perfect swing. In another embodiment, the swing which the user is compared to maybe a swing or style that the user has selected. For example, if a user wants to swing like a certain professional golfer, they could select that swing, and their swing would be compared to that professional golfer's swing. Furthermore, this could be applied to any other sports, including, but not limited to, baseball, football, swimming, etc. Further, the suggestion module 208 works with to provide learning tips, trick, or exercises to improve a user's swing.

The machine learning module 209 will determine where the problem areas are in the swing and the suggestion module 208 will find tips, trick, lessons, or exercises the user can do to improve the swing. The improvement material is stored in the suggestion database 205 where the improvement material (i.e. tips, tricks, lessons, or exercises) are associated with known problems or issues with a user's motion. For example, if it is identified that a user has too much weight on their back leg during a golf swing, the suggestion module may suggested tips or tricks that are known to help improve the flaw in the swing. In another embodiment, the suggestion module 208 is instructed by an instructor from the instructor device 400 on what material should be sent to the user and the user device 300 to help improve the user's motion. The machine learning module 209 compares user IMU data to other historical or known data to learn a user motion. For example, it would use a user's IMU data to learn the user's golf swing. The machine learning module 209 then uses the comparison to suggest improvements based on known instruction related to user data (suggestion database). Furthermore, in another embodiment suggestions can be provided to the user base on user data such as user preference based on user input or questionnaire. For example, the user maybe asked during a set up process asks like height, weight, body type, age, specific injury/impairment to recommend swing style. For example, a short guy with a big beer belly will not be able to or may not want to swing the same way a tall and fit person. Additionally, the sensors (in belt/waist shoulder etc.) calculate and determine the body shape or tendencies and recommend swing. The system can reinforce (good hits) or recommend changes (on bad hits). The Machine learning module additionally monitors suggestions or feedback from an instructor and store that data in the ML Database for future reference. The user device 300 may comprise of a computer, tablet, or cellphone. These devices are well known in the art and would comprise of a processor 302, a memory 302, a display 303, a communication device 304, image sensor 305, sensor database 306, GPS 307, base module 308, club-ball location module 309, a sensor location module 310, a play module 311, and a practice module 312. The processor 301 may include one or more general purpose processors (e.g., INTEL® or Advanced Micro Devices® (AMD) microprocessors, ARM) and/or one or more special purpose processors (e.g., digital signal processors, Xilinx® System On Chip (SOC) Field Programmable Gate Array (FPGA) processor, and/or Graphics Processing Units (GPUs)). The processor 301 may be configured to execute one or more computer-readable program instructions, such as program instructions to carry out any of the functions described in this description. The memory 302 is used to store information used in a computing device or related computer hardware. The memory 302 may be a semiconductor memory or metal-oxide-semiconductor (MOS) memory where data is stored within MOS memory cell. Examples of non-volatile memory are flash memory (used as secondary storage) and ROM, PROM, EPROM and EEPROM memory (used for storing firmware such as BIOS). Examples of volatile memory are primary storage, which is typically dynamic random-access memory (DRAM), and fast CPU cache memory, which is typically static random-access memory (SRAM) that is fast but energy-consuming, offering lower memory areal density than DRAM. The display 303 is integrated into the user device 300 and will include a means for user input either through a touch element (i.e. touch display) or other input methods. The display may be a liquid crystal display (LCD), in-plane switching liquid crystal display (IPS-LCD), organic light-emitting diode (OLED), or active-matrix organic light-emitting diode (AMOLED). The communication device 304 is used for communicating data and commands to the IMU 100 or to other devices that are part of the system such as the sports training system 200, or an instructor device 400. The communication can be done though a wired connection or wirelessly user well know wireless communication devices and protocols such as Bluetooth, NFC, Wi-Fi standards, or cellular. The image sensor 305 such as a CMOS, infrared sensor, or other types of optical sensor used for capturing images. The image sensor 305 on the user device 300 can be used to capture images of the user's motions and used with the IMU data and the analysis module 207 to overlay the IMU data. For example, a user may use the user device to record their swing while using the training system. That image or video is captured and stored with the IMU data in the IMU Database 204. The sensor database 306 is like the IMU Database 204 located on the Sports training system 200 but is instead located on the user device 300. The sensor database 306 stores all the IMU 100 data as well as sensor data that may be collected from devices on the user device 300 such as the image sensor 305. In another embodiment the sound data captured from a microphone on the of the user device 300 may also be stored and analyzed. Specifically, sound data could be used to analyze the sound of contact between two objects and if it were solid. For example, when a golf club hits a golf ball correctly it makes a unique sound, compared to when the golf club hits the golf ball off center. The GPS 307 or global positioning system can track the location of a user device 300. This data is used during the "play" function of a device. For example, when a user uses the system during a round of golf, not only can the system track the user's motion (i.e. swing), the system can further use the location of the user device to estimate how far the ball was hit and the trajectory. This data can be used to in association to the IMU 100 on a club to understand how far a user typically hits the ball with a specific club. It can also determine based on location if the ball was hit straight or not (i.e. slice or hook). The base module 308 when the user opens the sports training application on the user device 300. The base module 308 will then initiate all other associated module in the user device. First the base module 308 checks to see if any new sensors are within communication of the user device or if there are any sensors in the database. Because the system is meant to be a modular system, any number of IMUs 100 can be added or removed from the system at any time. If a new sensor is detected or no sensors are registered in the sensor database 306 the setup process begins and walks the user through a step-by-step process for adding or removing new IMUs 100. Once the setup is complete the user selects if they are practicing or playing. This will initiate the respective modules. The club-ball location module 309 is initiated as soon as the setup process is done and is initiated by the base module 308. The club-ball location module 309 uses the communication devices 106 on IMUs 100 in both shoes of the user and in a piece of sporting equipment such as a tennis racket or golf club. The module uses the communication devices 106 between at least three IMUs 100 to triangulate the locations of each. The use of triangulation using the signal from communication devices is well now in the art. For example, one possible method is to use the Bluetooth signal strength readings of three devices to calculate the position of one of the devices (https://cseweb.ucsd.edu/classes/fa06/cse237a/finalproj/almula.pd). The sensor location module 310 is used during the setup phase of the system and is initiated by the play or practice modules. The module is used to determine the location of the sensor based on the location of other sensors. The sensor location module 310 may use the same techniques described in the club-ball location module 309. In another embodiment the location of the IMUs 100 can be generally determined by polling the sensor database 306. The general location of the sensors could be determined during the setup up process, for example, locations of the sensors may be determined based on the location on the body (i.e. elbow, knee, hand, etc.). Knowing the location of the sensors either by triangulation or generally based on the position on the body will allow for more accurate measurements when analyzing a user movement or motion data, such as a swing. The play module 311 is initiated if the user selects play from the base module 308. The play module 311 is used when a user wants to user the IMUs 100 and sports training system 200 while playing a game. For example, if a user wanted to use the system to play a round of golf, the play module 311 would be initiated. The difference between using the IMUs 100 for play verses practice is that during a practice session you may use all the possible IMUs 100 that are available. A user during a practice session may have IMUs 100 across their entire body. While during play a user may not want to wear all the different sensor and only leverage specific sensors. For example, while practicing golf, a user may user all available sensors or IMUs 100 for the system which may include an IMU 100 in the golf club head, an IMU 100 in the user's shoes (i.e. insoles), and IMU 100 place around the body such as the knees, waist, hips, shoulders, elbow, incorporated in to user golf glove, or on the users head. While playing a round of golf all those devices attached to the body may be cumbersome. The play module 311 would only look for a few required sensors to make the system work and that are not cumbersome or incorporated into the user's clothes or gear. These IMUs 100 may include the golf club head, the user shoes (i.e. insoles), glove, and shirt. That way basic swing and movement information can still be tracked but not using all the information. Furthermore, the play module 311 would use the GPS 307 on the user device 300 to track the location of the user. In golf this could be used to track the distance and path of a user's ball. Because IMUs 100 are incorporated into a user's club, the system knows which club the user is using and can track how accurate the shots throughout the round are compared to the club used. The system could further use the club-ball location module 309 in real-time or during game play to provide the user feedback on correct club location while lining up for a shot. The practice module 312, as briefly described above would be initiated if a user wants to use the system during a practice session. During a practice session the practice module 312 would look for the maximum number of registered IMUs 100 that are registered or stored in the sensor data base 306. The practice module 306 may also initiate the image sensor 305 to be used to capture images of the user during their practice, for example while practicing a golf swing. The play module 311 and the practice module 312 are not limited to how may sensor each can user as described above. But in another embodiment the user would set up which sensor they would like to user during different situation in play. One user might prefer more sensors while playing a round of golf while a second user would prefer fewer. The instructor device 400 may be a cell phone, tablet, computer, or similar device and include a processor 401, a memory 402, a display 403, a communication device 404, an image sensor 405, instructor module 406. Further, the instructor device 400 would be a used by an instructor or a coach which allow them to review an athlete's motion who is using the sports training system 200. The instructor device 400 allows the instructor or coach to view motion data and analysis as well as provide manual feedback to the user device 300. The processor 401 may include one or more general purpose processors (e.g., INTEL® or Advanced Micro Devices® (AMD) microprocessors, ARM) and/or one or more special purpose processors (e.g., digital signal processors, Xilinx® System On Chip (SOC) Field Programmable Gate Array (FPGA) processor, and/or Graphics Processing Units (GPUs)). The processor 401 may be configured to execute one or more computer-readable program instructions, such as program instructions to carry out any of the functions described in this description. The memory 402 is used to store information used in a computing device or related computer hardware. The memory 402 may be a semiconductor memory or metal-oxide-semiconductor (MOS) memory where data is stored within MOS memory cell. Examples of non-volatile memory are flash memory (used as secondary storage) and ROM, PROM, EPROM and EEPROM memory (used for storing firmware such as BIOS). Examples of volatile memory are primary storage, which is typically dynamic random-access memory (DRAM), and fast CPU cache memory, which is typically static random-access memory (SRAM) that is fast but energy-consuming, offering lower memory areal density than DRAM. The display 403 is integrated into the instructor device 400 and will include a means for user input either through a touch element (i.e. touch display) or other input methods. The display may be a liquid crystal display (LCD), in-plane switching liquid crystal display (IPS-LCD), organic light-emitting diode (OLED), or active-matrix organic light-emitting diode (AMOLED). The communication device 404 is used for communicating data and commands to and from the user device 300 and the sports training system 200. The communication can be done though a wired connection or wirelessly user well know wireless communication devices and protocols such as Bluetooth, NFC, Wi-Fi standards, or cellular. The image sensor 405 such as a CMOS, infrared sensor, or other types of optical sensor used for capturing images. The image sensor 405 on the instructor device 400 can be used to capture images of the user's motions and used with the IMU data and the analysis module 407 to overlay the IMU data. The instructor module 406, is initiated by the instructor or coach and would allow the instructor to see the user's data and analysis. When initiated the instructor module 406 will communicate with the user device 300 and the sports training system 200 and receive the user's IMU data and analysis. The motion analysis it displayed to the instructor or coach along with the suggestions or feedback that would be provided to the user. The instructor or coach can then provide their own feedback by selecting from the suggestion database 204 or recommending suggestions provided by the suggestion module 208. In another embodiment, the coach's feedback may be customized. The instructor or coach may provide other tips or tricks not in the suggestion database.

FIG. 2 illustrates an exemplary machine learning (ML) database 203 for a given physical movement. The ML database 203 stores historical or all known IMU data which the machine learning module uses to compare to determine potential issues or flaws with a user's motion of swing. For example, the ML database 203 may story all example data for flaws in a golfer's swing and what the associated remedies would be to fix the flaw. If a golfer has too much weight on his back leg and is slicing the ball, the ML database would have IMU 100 data associated with this and the related fix, trick or exercise to fix the issue of too much weight on the back leg. Specifically, for the above-mentioned example, the ML database 203 would store data related to how much pressure should be measured on a pressure sensitive conductive sheet 108 in the sole of a user's shoe. This pressure measurement may be a range. If measured data from the IMU 100 is outside that range it can be determined there is a flaw. If the measured pressure is too high and outside the range it would suggest to much weight on the back leg of the user. The example above considers only one sensor to identify a problem, but in another embodiment a group of sensor data can be used to identify a flaw in the user's motion.

Figure 3:
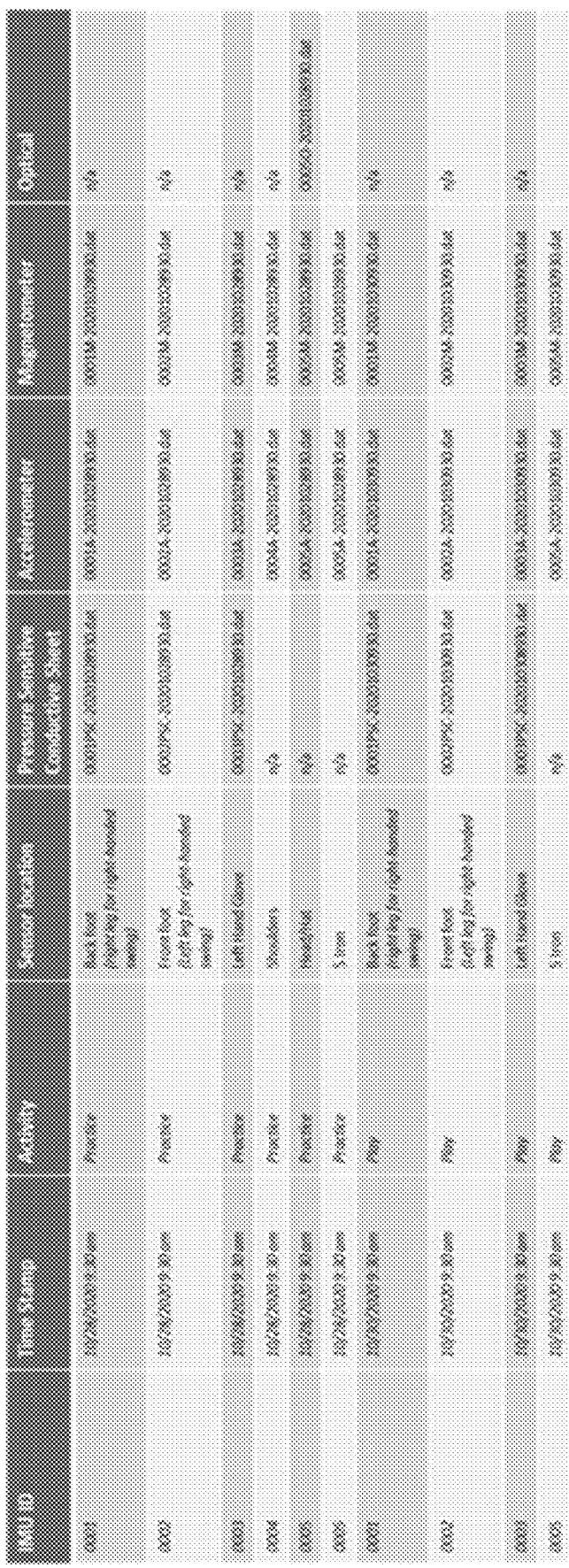
FIG. 3 illustrates an exemplary inertia measurement unit (IMU) database.

FIG. 3 illustrates an exemplary inertia measurement unit (IMU) database 204. The IMU database 204 stores all the IMU data received from either the user device 300 or the IMU 100. The stored data would include any sensor data, time stamps, user information, type of sport the user is using the IMU 100 for.

FIG. 4 illustrates an exemplary suggestion database 205. The suggestion database 205 stores suggested lessons, tips, tricks, corrections, and exercises to help correct a flaw or correction in a motion of a user (i.e. athlete). The suggestion data may come in the form of text, animation, or videos. For example, if data from the IMUs 100 determines that pressure on the back foot of a user at the end of their swing is higher than normal ranges it may be determined that they are leaving to much weight on their back leg during their swing. The suggestion database 205 has any number of tips, tricks, exercises, or lessons for correcting the issues. For example, there may be a video the user can watch of an instructor or coach providing tips on how to correct the issue.

Figure 5:
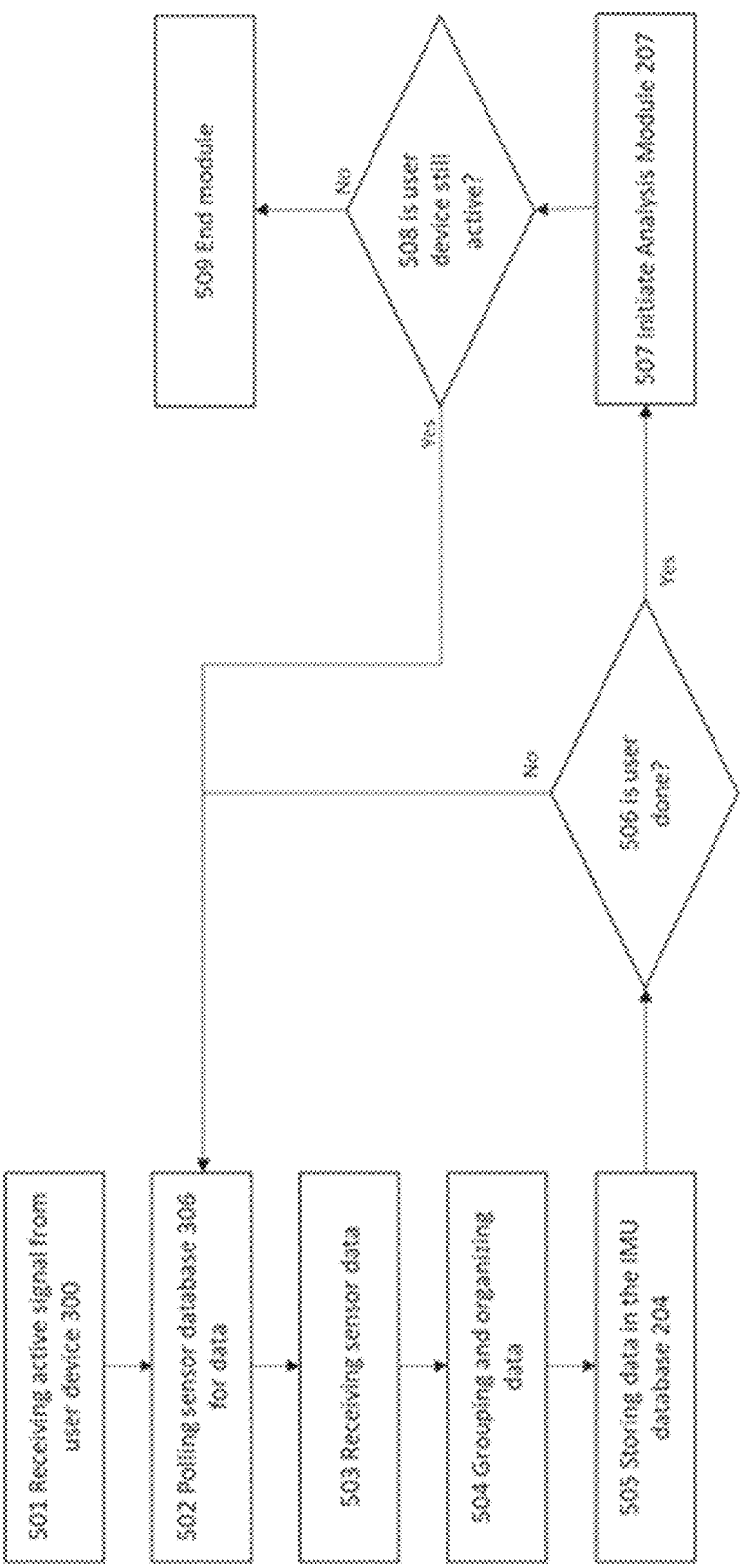
FIG. 5 is a flowchart illustrating an exemplary method for data collection regarding physical movement.

FIG. 5 is a flowchart illustrating an exemplary method for data collection regarding physical movement in accordance with execution of a data collection module 206. The data collection module 206 communicates with the user device 300 and the IMUs 100 to collect and organize the data in the IMU Database 204. The data collection module 206 begins with the module receiving a signal from the user device 300 that the user has initiated the system which will initiate the data collection module 206 at step 501. For example, this active signal may be generated when the user opens an app on the user device 300. Once the app loads it will connect with the sports training system 200 by sending the active signal which will allow the sports training system 200 to begin receiving data. Furthermore, the active signal can also be used for establishing a communications link directly between the user device 300 and the sports training system 200 for direct and secure data transfer. Once the data collection module 206 is active, the module begins to poll the sensor database 306 on the user device 300 for the most recent data, at step 502. The data is then received by the data collection module at step 503. The received data is then organized and grouped at step 504. The data that is being collected by the user device 300 from the IMUs 100 it is tracking the motion of user's movements such as a golf swing so data will be tracked over a period. There is also data coming from multiple IMUs 100 with any number of sensors. All that data needs to be grouped and organize so that analysis can be performed accurately over a period such the time it takes to swing a golf club. The data is then stored in the IMU database 204 at step 505. The module then checks to see the user is still swinging or if they are done at step 506. If the user is not done and plans on collecting more data, the module returns to step 502. In another embodiment, the system and module would be able to determine when a user starts a specific motion such as a golf swing by knowing what sport the user is playing and by monitoring the IMU data. Data is then stored once it is determined that the user has started the motion, i.e. golf swing. If the user is done with the motion, i.e. golf swing, then the analysis module 207 is initiated at step 507. Once the analysis module is initiated at step 507 the module determines if the user device 300 is still active or if they user done at step 508. If the user is not done the module returns to step 502, otherwise the module ends at step 509.

Figure 6:
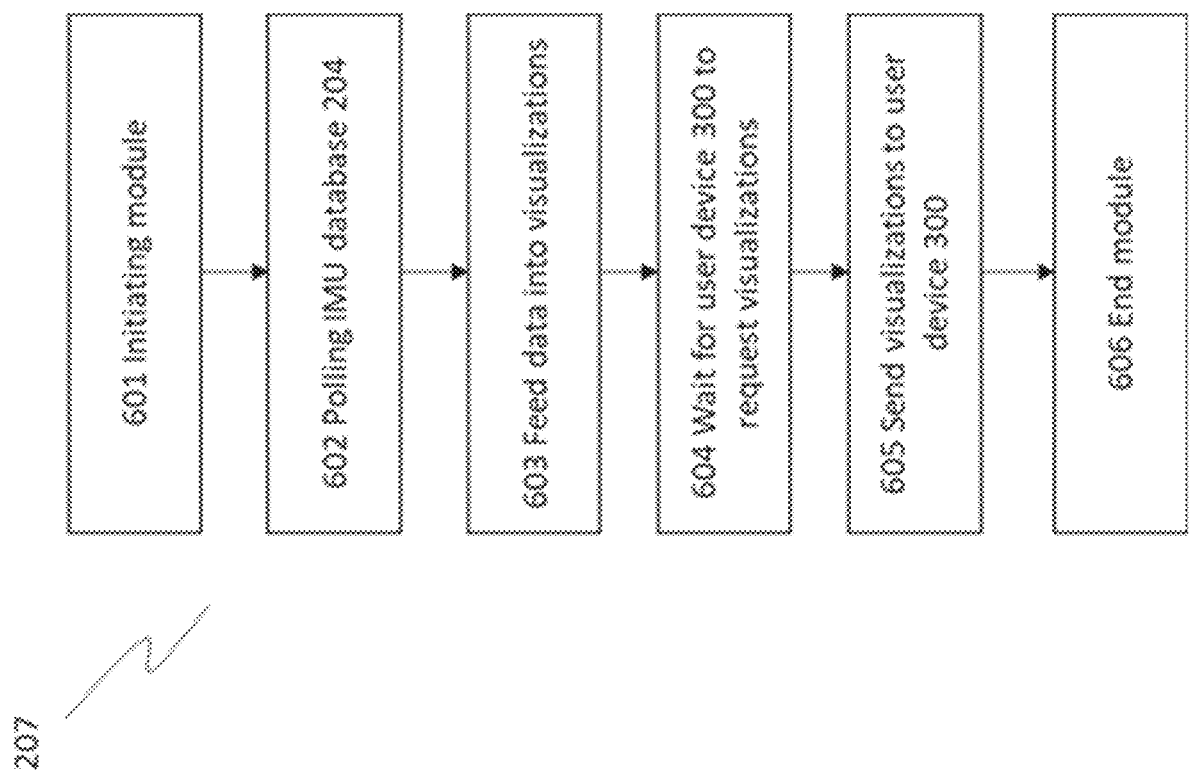
FIG. 6 is a flowchart illustrating an exemplary method for analyzing physical movement data.

FIG. 6 is a flowchart illustrating an exemplary method for analyzing physical movement data in accordance with execution of analysis module 207. The analysis module 207 begins with the data collection module 207 initiating it after collecting and organizing all the data in to the IUM database 204, at step 601. The analysis module 207 then beings polling the IMU database for the organized data, at step 602. The data is then feed into models, chart, histograms, tables, and other visualizations at step 603. The visualizations may be pre-configured and just need data feed to them. Methods of using preconfigured visualizations and feeding data into them are well known in the art. For example, IMU 100 data may be fed into a line graph that shows the pressure or weight on one foot during a motion, such as a golf swing. A user can then see how much pressure or weight was being distributed on that foot during their swing. The graph could also include normal ranges for how much weight that should be put on the foot during the swing. Specifically, the line graphs may have data from a pressure sensitive conductive sheet 108 that is placed in the sole of the shoe of the back leg of a right-handed user's golf swing. The X-axis of the graph would represent the time from the beginning of the user's swing to the end of their swing. The Y-axis would represent the pressure applied to the foot. A typical swing would normally show the user's weight or the pressure on the back foot somewhere in the middle of the y-axis as the user should have their weight distributed evenly at the beginning of their swing. As the swing begins the weight is distributed to the back leg and foot so the pressure would increase. Weight is then transferred to the user's front foot as the swing forward hitting the ball and following through. Another example of a visualization may be animations and 3D models. For example, a 3D model of a human figure performing a golf swing could have data overlaid on it such as a heat map of different datapoints. Pressure or movement data would be read if outside normal ranges for a swing while data within normal ranges is green. A user that performs a perfect swing would see a 3D animated representation of their golf swing and would show green for within normal ranges through the whole swing. The module then waits for a request from the user device 300 at step 604. The data is stored in memory on the sports training system 200 until the user device 300 requests it as not to overwhelm the user device with too much data as it would have limited processing power. When a request for the visualizations is received from the user device 300, the visualizations are then sent to the user device at step 605. Once the visualizations are sent the module ends until initiated again by the data collection module 206 to create new visualizations, at step 606.

Figure 7:
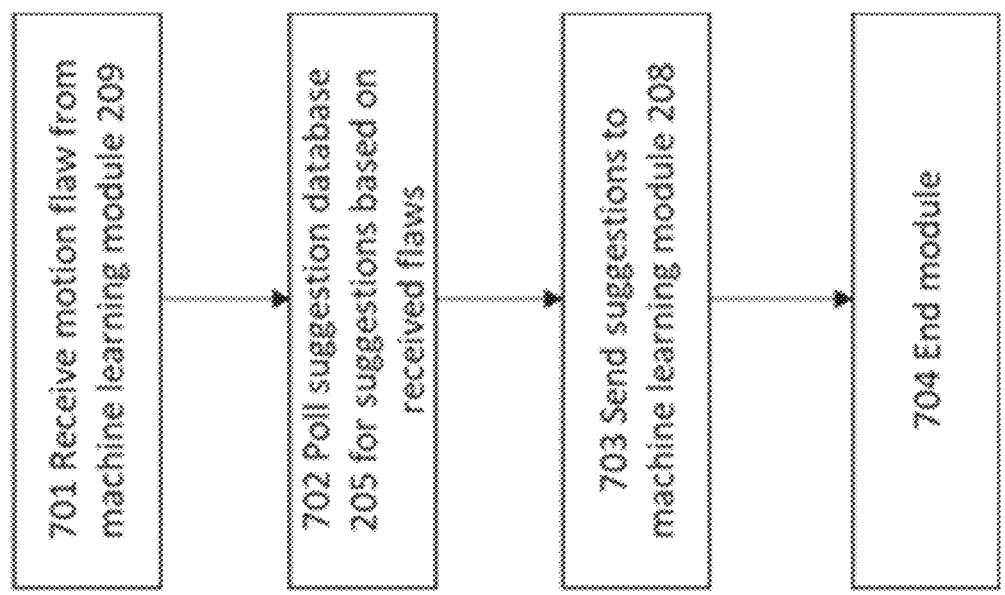
FIG. 7 is a flowchart illustrating an exemplary method for making learning-based suggestions regarding physical movement.

FIG. 7 is a flowchart illustrating an exemplary method for making learning-based suggestions regarding physical movement in accordance with execution of suggestion module 208. The suggestion module 208 begins with the receiving from the machine learning module 209 an identified flaw in a user's motion at step 701. For example, the machine learning module 209 may identify that the user has too much weight on their back foot on at the end of their swing in golf. Then the suggestion module 208 uses the received flaw to identify suggestions in the suggestion database 205, at step 702. There may be more than one suggestion for an identified flaw. Once flaws are identified they are sent back to the machine learning module 208 to be sent to the user device 300 and the instructor device 400.

Figure 8:
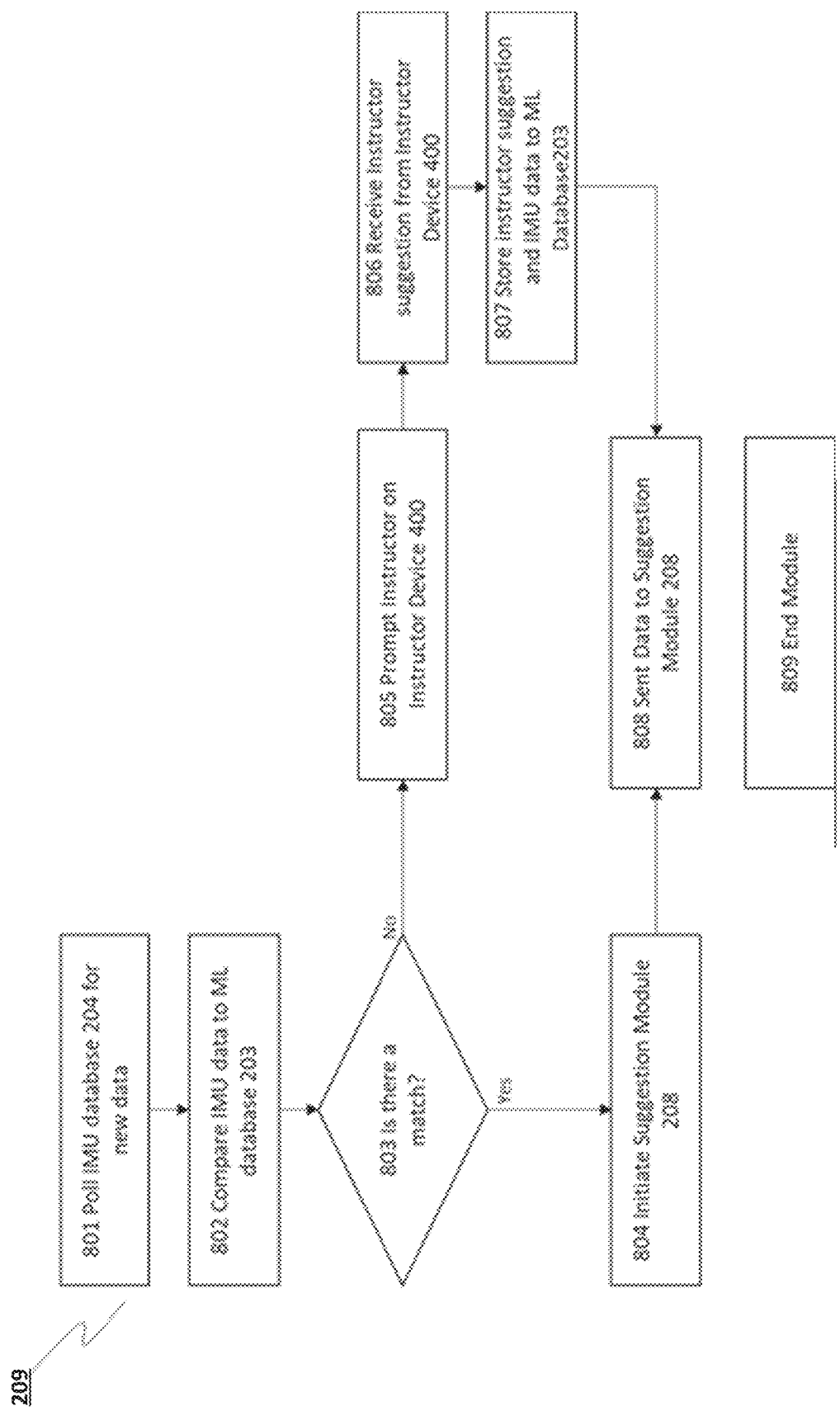
FIG. 8 is a flowchart illustrating an exemplary method for learning-based suggestion refinement.

FIG. 8 is a flowchart illustrating an exemplary method for learning-based suggestion refinement in accordance with execution of a machine learning module 209. The machine learning module 209 begins with the polling of the IMU database 204 for the most recent or new IMU data, at step 801. The new or recent IMU data is then compared to data in the ML database 203, at step 802. The ML database 203 stores data the machine learning module 209 can use to identify specific flaws in a user's swing and then automatically send the flaw to the suggestion module 208 which will then send suggests to improve the user's motion or swing. If there is a match with the IMU data and the ML database 203 at step 803 then the suggestion module is initiated. If at step 803 there is no match, then the instructor is prompted on the instructor device 400 at step 805. The purpose of prompting the instructor is because the machine learning module 209 cannot figure out what the flaw is in the user's motion or swing or that the individual's body type, or has a physical limitation due to injury, is not built for a normal swing, so the data is sent to the instructor. The instructor reviews the IMU data from the user and determines what the flaw(s) is(are) [or the individual's special needs are in the user's motion or swing and the instructor sends the determined flaw back to the machine learning module 209 as step 806. The instructor's determined flaw is then stored into ML database 203 with the IMU data at step 807, to ensure that the next time when similar IMU data is received that machine learning module 209 will recognize the flaw. The determined flaw is then sent to the suggestion module 208, at step 808. The data sent to the suggestion module 208 may be the flaw determined and polled from the ML database 203 or may be the determined flaw from the instructor. Once the data is sent to the suggestion module the machine learning module 209 ends at step 809. In some embodiments when the IMU data is compared to the ML database 203, the data is matched based on a threshold comparison, specifically the IMU data may not match the data in the ML database 203 exactly but may match within a threshold.

Figure 9:
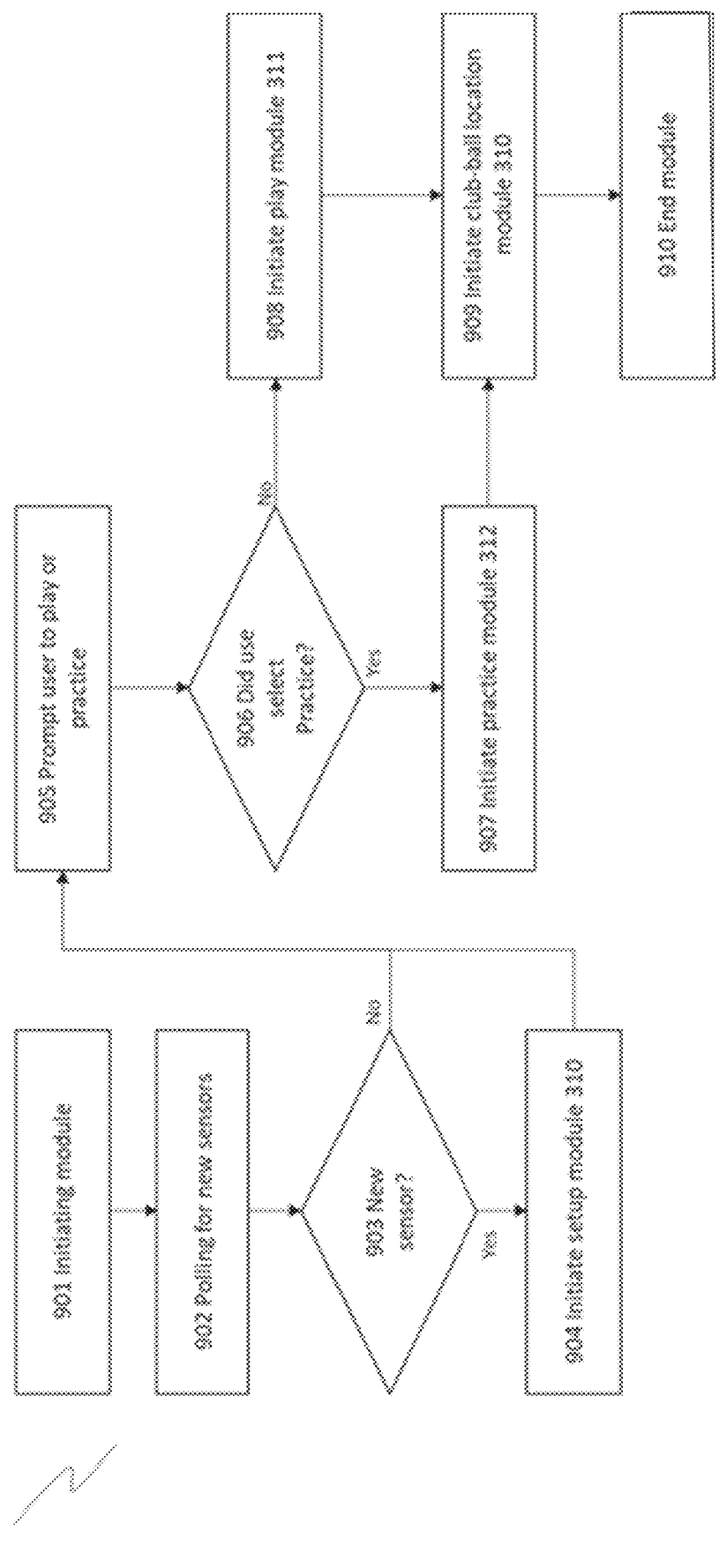
FIG. 9 is a flowchart illustrating an exemplary method for monitoring and analyzing physical movement.

FIG. 9 is a flowchart illustrating an exemplary method for monitoring and analyzing physical movement in accordance with execution of base module 308. The base module 308 begins when the user initiates the application on their user device 300 which initiates the module at step 901. The base module 308 then begins to poll to see if there are new sensors that have been connected or within proximity of the user device at step 902. Specifically, if there are any additional IMUs 100 that are not already in the sensor database 306. The module will do this by looking at the current sensors connected to the user device 300 and the sensors currently stored in the sensor database 306. Sensors may be connected using known communication methods such as Bluetooth, NFC, or other methods of low power communications. If new sensors are detected, at step 903 the setup module 310 is then initiated at step 904. If no new sensors are detected at step 903 then the user is prompted if they are using the application to play or to practice at step 905. For example, when the golfer wants to use the application to practice their golf swing at the driving range they would select the practice option, while when the user wants to play a round of golf they would select the play option. The difference of the two options, play vs. practice would determine which sensors the system would use. For example, for practice mode the system would not need to use the user device 300 GPS 307 but might leverage additional sensors when compared to when playing. At step 906 it is determined if the user selected "practice", if yest then the practice module 312 is initiated at step 907. If the user selects "play" instead of "practice" the play module 311 is initiated at 908. Once the play module 311 or the practice module 312 the club-ball location module 310 is initiated at step 909. At this point all required modules for the user device 300 have been initiated and the module ends at 910.

Figure 10:
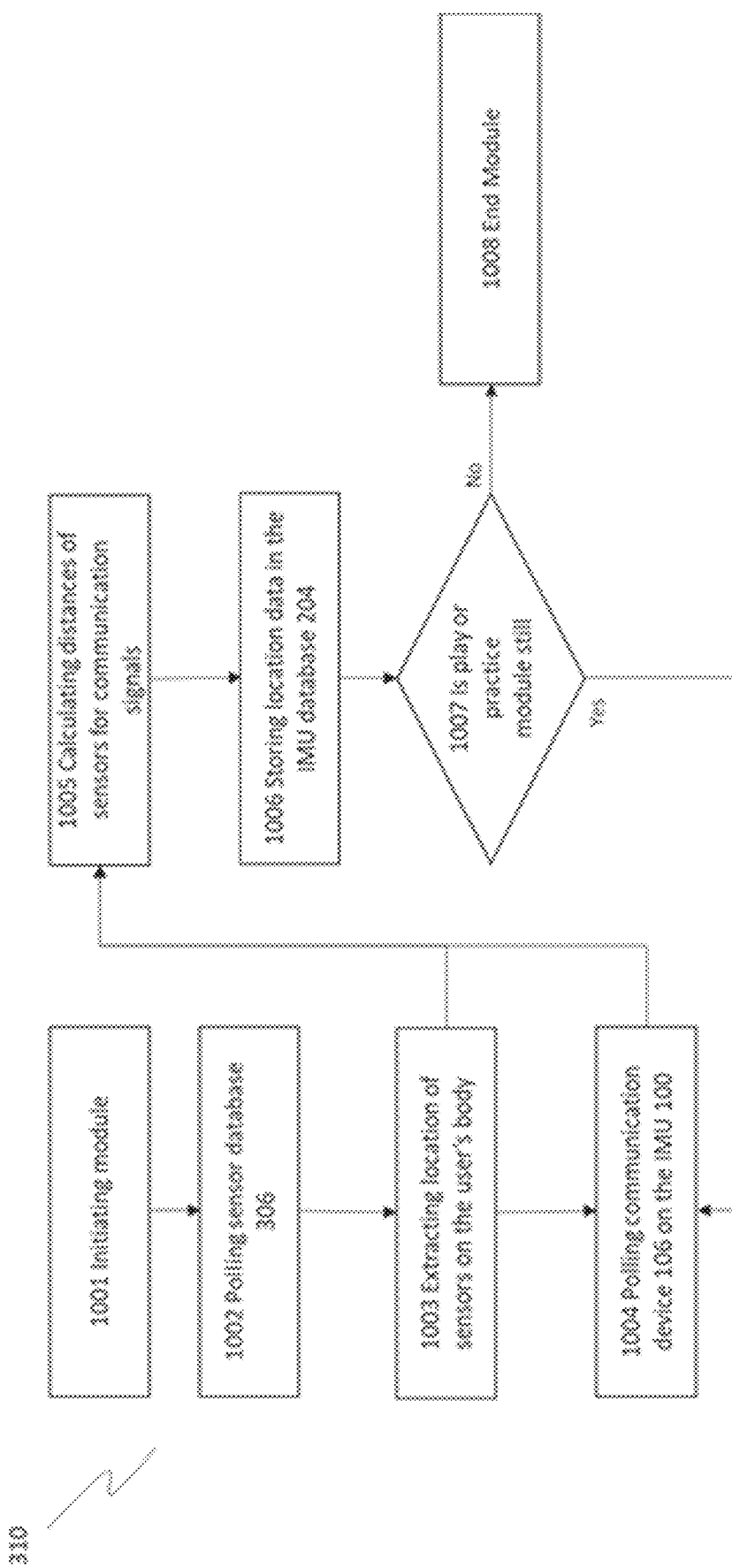
FIG. 10 is a flowchart illustrating an exemplary method for locating and polling movement sensors.

FIG. 10 is a flowchart illustrating an exemplary method for locating and polling movement sensors in accordance with execution of sensor location module 310. The sensor location module begins with the module being initiated by either the play module 311 or the practice module 312 at step 1001. The sensor database 306 is then polled to determine how many and which sensors are already connected to the user device 300 as step 1002. The sensor database 306 stores the type of sensors or IMUs 100 that are connected to the system and the user device 300. Furthermore, the approximate location of the sensor on the user's body is also stored during setup process, for example, the location may be the foot, club, or head. The location of the sensors is extracted at step 1003. Once the general location on a user's body is determined the communication device on 106 on the IMU 100 is the polled for its signal data at step 1004. The signal data is then used to calculate the exact location of each sensor in relation to at least two other sensors at step 1005. Methods for calculating the exact location of a device using communications data is well known in the art. For example, leveraging the signal between three different devices, the signal strength can be used to calculate the location of each sensor from one another using triangulation. The location data is then stored in the IMU Database 204 at step 1006. The location data could also be stored locally in the sensor database 306 if there for some reason is not a connection to the sports training system 200. At step 1007 the module determines if the play module 311 or practice module 312 is still active. If the play module 311 or practice module 312 is still active the location data of all sensors is continuously calculated so the module returns to step 1004. The location of different sensors is needed to better understand the movement of a user's body. Furthermore, a sensor may be in the head of a golf club or in a bat that can help track the user's swing. If the play module 311 or practice module 312 are no longer active the module ends at step 1008.

Figure 11:
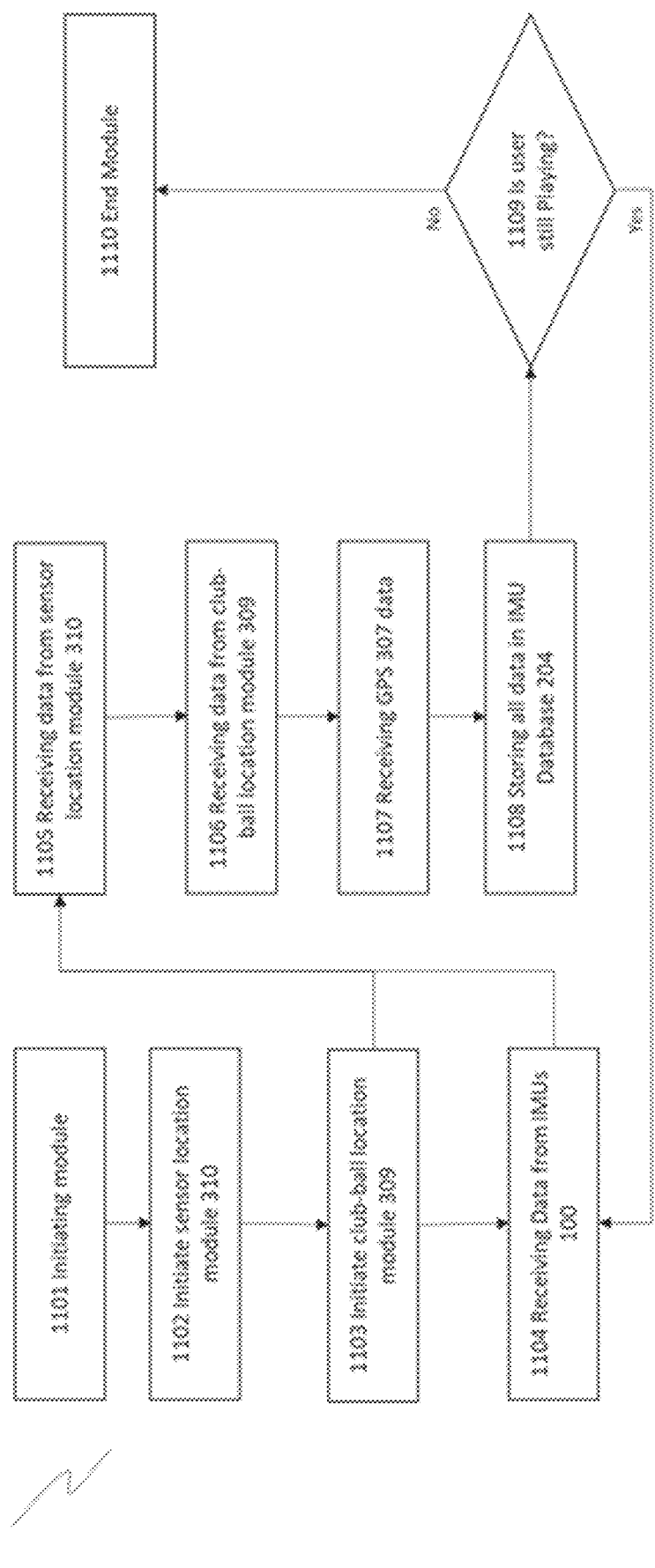
FIG. 11 is a flowchart illustrating an exemplary method for play monitoring and analysis.

FIG. 11 is a flowchart illustrating an exemplary method for play monitoring and analysis in accordance with execution of play module 311. The play module 311 begins with the base module 308 initiating the module when a user selects the option to "Play" at step 1101. The sensor location module 310 is then initiated at step 1102. This allows the play module 311 to determine the exact location and which sensors are currently being used. For example, a user may only use a limited number of sensors when playing a round of golf rather than all possible sensors when practicing. Furthermore, while playing a round of golf a user may not want to wear so many sensors that could be cumbersome. The club-ball location module 309 is also initiated which will help determine when used for golfing will determine if the placement of the ball and club are correct prior to a user's swing, at step 1103. Data is then received from the IMUs 100 that are connected and being used at step 1104. Data is also received from the sensor location module 310 at step 1105. Data is also received from the club-ball location module 309 at step 1106. GPS data from the GPS 307 on the user device 300 is also receive at step 1107. GPS data can be used to track a user's performance and movements during play. For example, when a user plays a round of golf the GPS data can be used to determine how far a user hits a ball based on where they are when they swing. All the sensor data including GPS data, IMU data, location data is then stored in the IMU database 306 at step 1108. Data could also be stored in the sensor database 306 before being sent to the sports training system 200 and the IMU database 204. It is then determined if the player is still playing or not at step 1109. If the user is still playing, then the system continues to receive data and returns to step 1104. If the user is no longer playing, then the module ends at step 1110.

Figure 12:
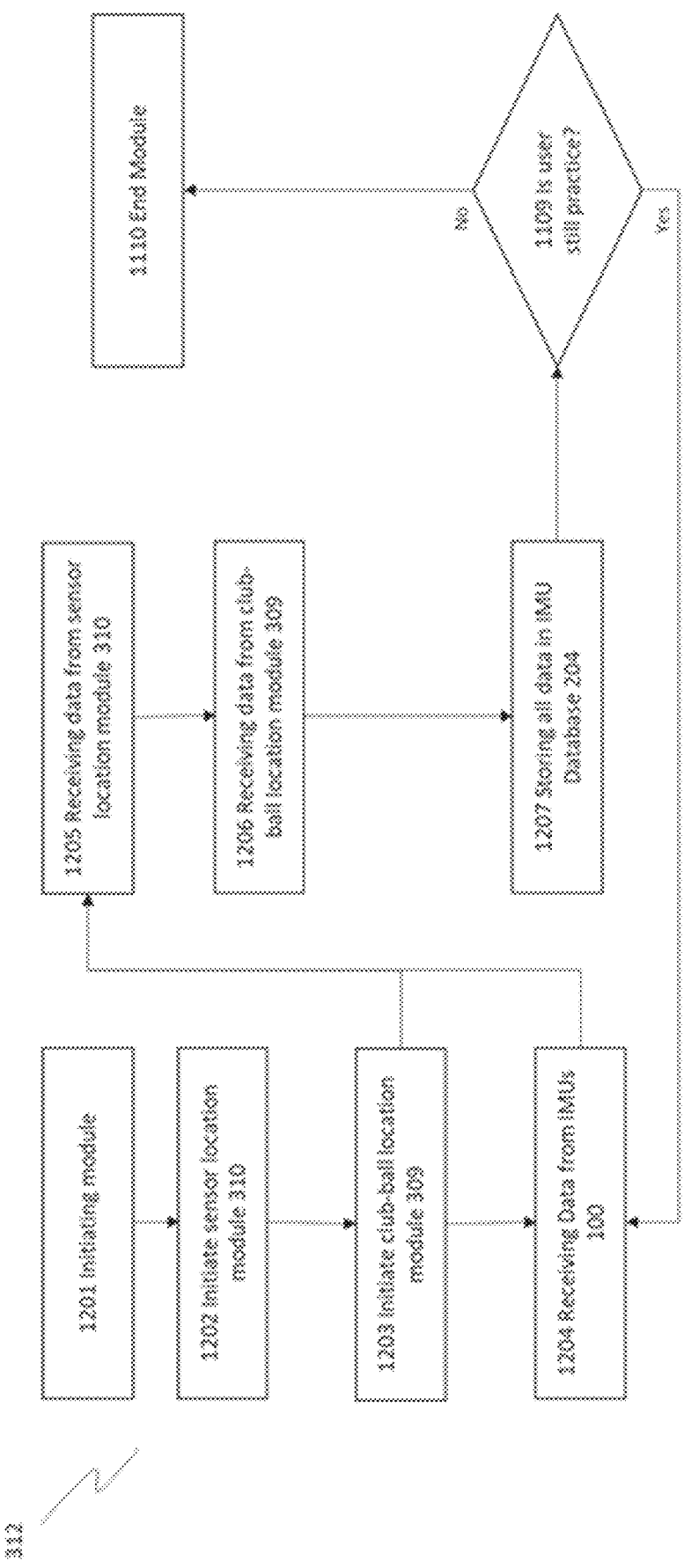
FIG. 12 is a flowchart illustrating an exemplary method for practice monitoring and analysis.

FIG. 12 is a flowchart illustrating an exemplary method for practice monitoring and analysis in accordance with execution of practice module 312. The practice module 312 begins with the base module 308 initiating the module when a user selects the option to "practice" at step 1201. The sensor location module 310 is then initiated at step 1202. This allows the practice module 312 to determine the exact location and which sensors are currently being used. For example, a user may use all available sensors when practicing getting a better understanding and analysis of their motion or swing. The club-ball location module 309 is also initiated which will help determine when used for golfing will determine if the placement of the ball and club are correct prior to a user's swing, at step 1203. Data is then received from the IMUs 100 that are connected and being used at step 1204. Data is also received from the sensor location module 310 at step 1205. Data is also received from the club-ball location module 309 at step 1206. All the sensor data including IMU data, and sensor location data is then stored in the IMU database 306 at step 1207. Data could also be stored in the sensor database 306 before being sent to the sports training system 200 and the IMU database 204. It is then determined if the player is still practicing or not at step 1208. If the user is still practicing the system continues to receive data and returns to step 1204. If the user is no longer playing, then the module ends at step 1209.

Figure 13:
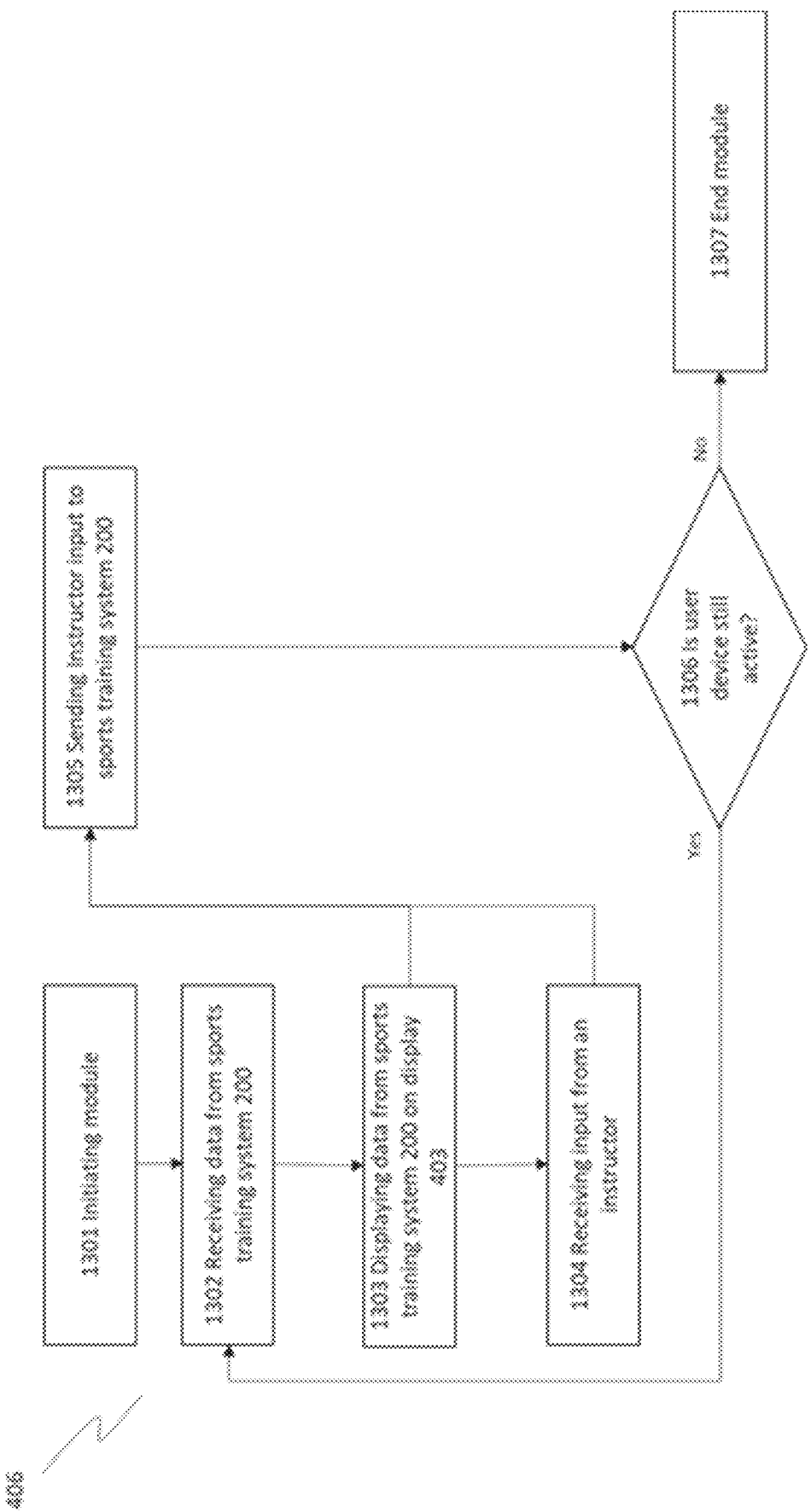
FIG. 13 is a flowchart illustrating an exemplary method for instruction management.

FIG. 13 is a flowchart illustrating an exemplary method for instruction management in accordance with execution of instructor module 406. The instructor module 406 begins with the module being initiated either by the instructor opening an application on the instructor device 400 or by a prompt from the sports training system 200 at step 1301. The prompt may come to the instructor device 400 in an alert or notification. For example, if the machine learning module 209 can determine a flaw while a user is practicing and the instructor isn't present it would prompt the instructor to determine the flaw to help further improve the machine learning algorithm and data. Once the instructor module 406 has been initiated the module receives data sent from the sports training system 200 at step 1302. The received data would be the IMU data from the user's IMUs 100. In another embodiment, the data received are recommendations from the machine learning module 209 on the closest matches to the IMU data for potential flaw in a user's motion. The received data is then displayed on the on the instructor device 400 display 403. The instructor would see analyzed data of the user's motion or swing and would be asked to provide feedback or to identify the flaw. The instructor could even provide suggested remedies, exercises, or lessons to improve the flaw. The instructor's input would then been received at step 1304. The instructor's input would then be sent back to the sports training system 200 at step 1305. The instructor module 406 would then communicate with the user device 300 to determine if the user is still actively using the system at step 1306. If the user is still active the module would return to step 1302 to continue to receive data from the sports training system 200 and the instructor would continue to provide feedback. Whereas if the user is no longer actively practicing or playing, then the instructors is no longer needed, and the module ends at step 1307.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. A system for customizing movement feedback for integrated sport training, the system comprising:
   a database that stores one or more models regarding different types of motions associated with a plurality of different activities, each model including a set of measurements associated with one or more user that have different physical limitations;
   a plurality of different types of sensors configured to measure a parameter at a location on a body of a user; and
   a computing device configured to:
      receive a plurality of measurements from the sensors during performance of a motion by the user;
      determine one or more locations of the sensors during the motion, wherein at least one of the locations is determined based on triangulation;
      apply machine learning to the received measurements to identify the activity associated with the motion, to identify a physical limitation of the user, and to recognize a deviation in the motion, wherein the machine learning is applied in accordance with the model associated with the identified activity and physical limitation; and
      generate one or more customized feedback communications based on the identified deviation from the stored set of measurements associated with the applied model.

2. The system of claim 1, wherein the locations of the sensors include locations on or within equipment held by or worn on the body of the user, the equipment including at least one of a golf club head, shoe, or glove.

3. The system of claim 1, wherein the triangulation is based on one or more communication signals between the sensors.

4. The system of claim 1, wherein the computing device generates the customized feedback communications based on stored instructor feedback provided to a machine learning module.

5. The system of claim 1, wherein the sensors include a gyroscope that detect an amount of rotation at the respective location on the body of the user, and wherein the computing device generates the customized feedback further based on the detected amount of rotation.

6. The system of claim 1, wherein the customized feedback includes a visualization that includes a 3D mapping of the motion by the user.

7. The system of claim 6, wherein the visualization includes at least one of a chart, a graph, or a heatmap that uses one or more colors or one or more color intensities to represent an extent of the identified deviations during the motion by the user.

8. The system of claim 1, wherein the computing device further receives user input regarding one or more of height, weight, body type, age, injury, or impairment of the user, and wherein the computing device generates the customized feedback communications based on the received user input.

9. The system of claim 1, wherein the measurements are associated with time stamps during the motion by the user.

10. The system of claim 1, wherein the measurements by the sensors are further used to determine a body shape or tendency of the body of the user.

11. A method for customizing movement feedback for integrated sport training, the method comprising:
   storing one or more models regarding different types of motions associated with a plurality of different activities, each model including a set of measurements associated with one or more users that have different physical limitations;
   receiving a plurality of measurements from a plurality of different types of sensors that measure a parameter at a location on a body of a user during performance of a motion by the user;
   determining one or more locations of the sensors during the motion, wherein at least one of the locations is determined based on triangulation;
   applying machine learning to the received measurements to identify the activity associated with the motion, to identify a physical limitation of the user, and to recognize a deviation in the motion, wherein the machine learning is applied in accordance with the model associated with the identified activity and physical limitation; and
   generating one or more customized feedback communications based on the identified deviation from the stored set of measurements associated with the applied model.

12. The method of claim 11, wherein the locations of the sensors include locations on or within equipment held by or worn on the body of the user, the equipment including at least one of a golf club head, shoe, or glove.

13. The method of claim 11, further comprising performing the triangulation based on one or more communication signals between the sensors.

14. The method of claim 11, wherein generating the customized feedback communications based on stored instructor feedback provided to a machine learning module.

15. The method of claim 11, wherein the sensors include a gyroscope that detect an amount of rotation at the respective location on the body of the user, and wherein generating the customized feedback is further based on the detected amount of rotation.

16. The method of claim 11, wherein the customized feedback includes a visualization that includes a 3D mapping of the motion by the user.

17. The method of claim 16, wherein the visualization includes at least one of a chart, a graph, or a heatmap that uses one or more colors or one or more color intensities to represent an extent of the identified deviations during the motion by the user.

18. The method of claim 11, further comprising receiving user input regarding one or more of height, weight, body type, age, injury, or impairment of the user, and wherein generating the customized feedback communications is based on the received user input.

19. The method of claim 11, wherein the measurements are associated with time stamps during the motion by the user.

20. The method of claim 11, wherein the measurements by the sensors are further used to determine a body shape or tendency of the body of the user.

21. A non-transitory, computer-readable storage medium, having embodied thereon a program executable by a processor to perform a method for customizing movement feedback for integrated sport training, the method comprising:

storing one or more models regarding different types of motions associated with a plurality of different activities, each model including a set of measurements associated with one or more users that have different physical limitations;

receiving a plurality of measurements from a plurality of different types of sensors that measure a parameter at a location on a body of a user during performance of a motion by the user;

determining one or more locations of the sensors during the motion, wherein at least one of the locations is determined based on triangulation;

applying machine learning to the received measurements to identify the activity associated with the motion, to identify a physical limitation of the user, and to recognize a deviation in the motion, wherein the machine learning is applied in accordance with the model associated with the identified activity and physical limitation; and generating one or more customized feedback communications based on the identified deviation from the stored set of measurements associated with the applied model.

* * * * *